United States Patent

Schaefer et al.

(10) Patent No.: US 10,398,217 B2
(45) Date of Patent: Sep. 3, 2019

(54) PERSONAL HYGIENE DEVICE HAVING TREATMENT-FORCE-MEASUREMENT UNIT

(71) Applicant: Braun GmbH, Kronberg (DE)

(72) Inventors: Norbert Schaefer, Frankfurt (DE); Martin Haas, Steinback (DE); Daniel Dietzel, Kelkheim (DE); Christian Probst, München (DE); Stefan Meier, München (DE)

(73) Assignee: BRAUN GMBH, Kronberg (DE)

( * ) Notice: Subject to any disclaimer, the term of this patent is extended or adjusted under 35 U.S.C. 154(b) by 428 days.

(21) Appl. No.: 15/153,697

(22) Filed: May 12, 2016

(65) Prior Publication Data

US 2016/0331119 A1 Nov. 17, 2016

(30) Foreign Application Priority Data

May 12, 2015 (EP) ..................................... 15167363

(51) Int. Cl.
*A46B 15/00* (2006.01)
*A61C 17/22* (2006.01)
*A46B 9/04* (2006.01)

(52) U.S. Cl.
CPC ............ *A46B 15/0012* (2013.01); *A46B 9/04* (2013.01); *A46B 15/0044* (2013.01); *A61C 17/221* (2013.01)

(58) Field of Classification Search
CPC ............ A46B 15/0012; A46B 15/0002; A61C 17/221; B26B 21/52
See application file for complete search history.

(56) References Cited

U.S. PATENT DOCUMENTS

| 3,420,222 A * | 1/1969 | Noe ..................... A61B 5/1101 33/501.04 |
| 4,698,869 A | 10/1987 | Mierau et al. |
| 5,493,747 A | 2/1996 | Inakagata et al. |
| 7,281,289 B1 | 10/2007 | Mirza |
| 8,544,131 B2 * | 10/2013 | Braun ................ A46B 15/0002 15/105 |
| 2011/0314677 A1 * | 12/2011 | Meier .................. A46B 5/0062 30/41.8 |

OTHER PUBLICATIONS

"Magnetic Permeability", Encyclopaedia Britannica, https://www.britannica.com/science/magnetic-permeability, accessed Sep. 1, 2018.*
International Search Report with Written opinion, dated Jul. 8, 2016, 10 pages.
Dan Mihai Stefanescu: "Inductive Force Transducers", Jan. 1, 2011 (Jan. 1, 2011), Handbook of Force D3 Transducers, Springer, De, pp. 73-86, XP009186441, ISBN: 978-3-642-18296-9.

* cited by examiner

*Primary Examiner* — Laura C Guidotti
(74) *Attorney, Agent, or Firm* — Vladimir Vitenberg

(57) ABSTRACT

A personal hygiene device, in particular a toothbrush, has a handle, a treatment head mounted for relative movement with respect to the handle against a spring force when a treatment force is applied in at least one direction onto the treatment head, a treatment-force-measurement unit for determining the applied treatment force comprising an electrically powered coil, a coil core element, and a control circuit for determining a parameter indicative of the inductance of the coil, wherein the coil core element is arranged to be moved with respect to the coil when the treatment head is moved.

19 Claims, 4 Drawing Sheets

PERSONAL HYGIENE DEVICE HAVING TREATMENT-FORCE-MEASUREMENT UNIT

FIELD OF THE INVENTION

The present invention is concerned with a personal hygiene device having a treatment-force-measurement unit, in particular wherein the treatment-force-measurement unit is arranged to measure the treatment force applied at a treatment head that is mounted for movement under application of a treatment force relative to a handle of the personal hygiene device.

BACKGROUND OF THE INVENTION

It is known that a toothbrush can be equipped with a treatment-force-measurement unit for determining when a treatment force with which a toothbrush head is pushed against the teeth reaches a predetermined treatment force threshold value. Such a treatment-force-measurement unit may comprise a strain gauge sensor. It is also known that reaching the predetermined treatment force threshold value can be visually indicated. DE 34 146 23 C1 generally discusses such a toothbrush.

It is an object of the present disclosure to provide a personal hygiene device with at least an alternative treatment-force-measurement unit than in the known devices.

SUMMARY OF THE INVENTION

In accordance with one aspect there is provided a personal hygiene device, in particular a toothbrush, having a handle, a treatment head mounted for relative movement with respect to the handle against a spring force when a treatment force is applied in at least one direction onto the treatment head, a treatment-force-measurement unit for determining the applied treatment force comprising an electrically powered coil, a coil core element, and a control circuit for determining a parameter indicative of the inductance of the coil, wherein the coil core element is arranged to be moved with respect to the coil when the treatment head is moved.

BRIEF DESCRIPTION OF THE DRAWINGS

The present disclosure will be further elucidated by a detailed description of example embodiments with reference to figures. In the figures

DETAILED DESCRIPTION OF THE INVENTION

In the present disclosure, reference is mainly made to an electric toothbrush as personal hygiene device. This shall not exclude that other personal hygiene devices are also contemplated such as manual toothbrushes, safety razors, electric shavers, massage devices, epilators, etc., which devices can benefit in various ways from a determination of a treatment force applied at a treatment head, in particular by indicating a correct range of the applied treatment force for achieving good treatment results.

A personal hygiene device as proposed is equipped with a treatment-force-measurement unit that relies on the changing inductance ("inductance" shall here include the (complex) impedance) of a coil when the coil and a coil core element are moved relatively to each other in close proximity (in particular where the coil core element is relatively moved in and out of a coil hollow) as a result of the applied treatment force. A control circuit measures a parameter (e.g. a voltage or a current) that is indicative of the inductance of the coil and can thus determine changes in the coil inductance. As the application of a treatment force at the treatment head of the personal hygiene device leads to a deflection of the treatment head (against a spring force), the deflection is used to cause the relative movement of the coil and the coil core element. This leads to a change in the coil inductance, which is measured as described and can be related to the treatment force, e.g. by calibration. In some embodiments, the control circuit is calibrated, e.g. at the plant of the manufacturer, to easily relate the measured parameter to a precise absolute value of the applied treatment force. The knowledge of the value of the applied treatment force allows for improving at least one of various aspects of the usage of the personal hygiene device, which aspects may range from a mere indication of the currently applied treatment force (e.g. by a green light emission element to indicate correct treatment force, a red light emission element to indicate too high treatment force, and optionally a further light emission element, e.g. an orange light emission element, to indicate too low treatment force) to providing a statistical report of the treatment force applied in the course of a treatment session or during a certain time span, e.g. two weeks. Additionally or alternatively tips on how to change usage of the personal hygiene device for ideally improved treatment results may be provided.

Figure 1:
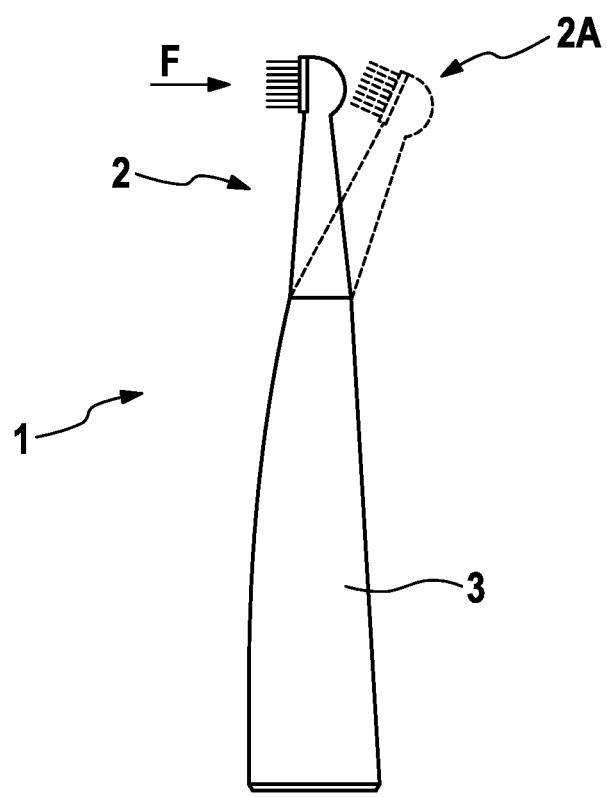
FIG. 1 is a depiction of an example personal hygiene device, here realized as an electronic toothbrush.

FIG. 1 is a depiction of an example personal hygiene device 1, here without limitation shown as an electric toothbrush. The personal hygiene device 1 has a treatment head 2 that is mounted at a handle 3 so that a treatment force F acting onto the treatment head 2 in at least one direction leads to a movement of the treatment head 2 relative to the handle 3 (indicated by a deflected treatment head 2A shown in dashed lines, where the deflection is exaggerated for sake of visualization). In some embodiments, treatment forces applied in various directions lead to a deflection of the treatment head, e.g. because the treatment head is coupled to the handle by means of a ball joint or the like. The movement of the treatment head 2 relative to the handle 3 may be a movement around a pivot point, may be an elastic deflection or any other type of relative movement. A spring force acting against the movement or deflection may be provided by a resilient element (e.g. a spring) arranged between the treatment head and the handle or the spring force may be generated due to an elastic deformation of a part of the handle 3 or treatment head 2.

Figure 2:
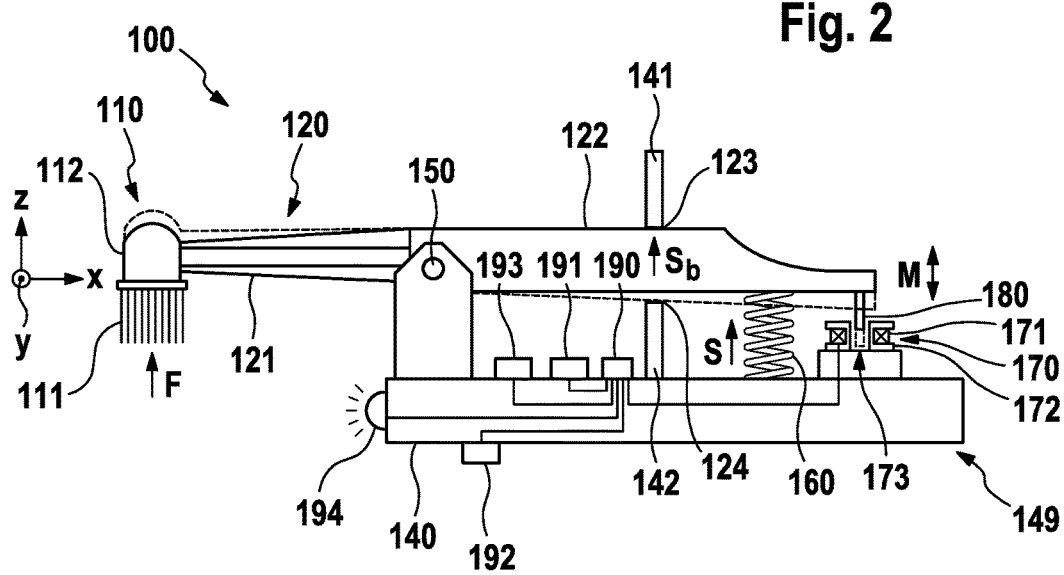
FIG. 2 is a schematic depiction of an example embodiment of a personal hygiene device in accordance with the present disclosure.

FIG. 2 is a schematic simplified depiction of a personal hygiene device 100 comprising a treatment head 120 that is pivotably mounted at a handle 140 (here for sake of simplicity just indicated by a wall element). A coordinate system having x-, y-, and z-axis is shown as reference (the y-axis extends into the paper plane). The treatment head 120 is arranged to be moveable around a pivot axis 150 (here extending in y direction) against a spring force S provided by a resilient element 160 (which may have a linear spring constant at least in the range of forces that typically occur in a treatment session—i.e. treatment forces in the range of between about 0.5 Newton and about 7 Newton) arranged between the handle 140 and the treatment head 120. Provision of a pivot axis shall be considered as non-limiting and other linkages between treatment head and handle are considered as well. A treatment force F being applied at the treatment head 120 will cause such a deflection (here, the treatment force is applied at a front portion 110 of the treatment head 120). In order to move the treatment head 120 around the pivot axis 150, the applied treatment force F needs to have at least one force component that acts as a torque (i.e. moment of force) around the pivot axis 150. With reference to the coordinate system, the treatment force F must initially have a component in the z direction; generally, the treatment force F must have a component that lies in a plane to which the pivot axis 150 is normal and which component is perpendicular to a radial line originating at the pivot axis and extending in said plane. Thus, the term "treatment force" in the present disclosure shall mean a force that has such a force component that can turn the treatment head 120 around the pivot axis 150 and all force values given herein, if not stated otherwise, relate to this force component. The personal hygiene device 100 generally extends in a longitudinal direction (here the x direction) between a first end (front portion 110 of the treatment head 120) and a second end (back end 149 of the handle 140).

The front portion 110 of the treatment head 120 is here indicated as a brush head for use with an electric toothbrush. The front portion 110 has here a carrier element 112 (which may be mounted for movement relative to the treatment head 120) on which treatment elements 111 (here: cleaning elements such as tufts made from nylon filaments or elastomeric cleaning fingers etc.) are mounted.

The treatment head 120 may have a front arm 121 that extends from the pivot axis 150 to the front portion 110 and an arm element 122 that extends from the pivot axis 150 towards the back end of the handle 140. In the shown embodiment, the arm element 122 tapers towards its back end; this shall be understood as just a non-limiting design option). A resilient element 160 (here indicated as a mechanical coil spring) is arranged between the handle 140 and the treatment head 120, here between handle 140 and arm element 122 of the treatment head 120. In some embodiments, a first stopper 141 that is fixedly mounted with respect to the handle 140 is arranged so that a rest position of the treatment head 120 is defined when no treatment force F is applied. In the rest position, the treatment head 120 abuts the first stopper 141 at abutment point 123. The rest position may be mechanically calibrated in a manner so that no biasing spring force $S_b$ acts against the treatment head 120. In some embodiments, the rest position may be defined such that a biasing spring force $S_b \neq 0$ Newton (N) acts against the treatment head 120 towards the first stopper 141 so that only an applied treatment force F that overcomes this biasing spring force $S_b$ (F>$S_b$) will move the treatment head 120 away from the first stopper 141 around the pivot axis 150. The biasing spring force $S_b$ may be set such that a treatment force F between 0.5 N and 2 N starts to move the treatment head 120. The biasing spring force $S_b$ may in particular be set such that a treatment force F of at least 0.5 N, 0.75 N, 1.0 N, 1.25 N, 1.5 N, 1.75 N, or 2.0 N starts to move the treatment head 120.

The shown embodiment shall not exclude that at least a front portion of the treatment head is arranged to be repeatedly detachable from the handle and that at least a portion of the arm element 122 is non-detachably connected with the handle. The arm element 122 may then become connected with the treatment head 120 once it become attached to the handle 140 and then moves when the applied treatment force F deflects the treatment head 120.

In some embodiments, a second stopper 142 is mounted fixedly with respect to the handle 140 and defines a maximum deflection position of the treatment head 120. As indicated by dashed lines, the maximally deflected treatment head 120 abuts the second stopper 142 at abutment point 124. The first stopper 141 and the second stopper 142 define a maximum deflection range around the pivot axis 150 out of the rest position. The maximum deflection position provided by the second stopper 142 may be calibrated to relate to an applied treatment force in the range of between 3.5 N to 7.5 N and may in particular be set to 3.5 N, 4.0 N, 4.5 N, 5.0 N, 5.5 N, 6.0 N, 6.5 N, 7.0 N, or 7.5 N.

The personal hygiene device 100 further comprises a coil 170 that can be electrically powered by a control circuit 190, which control circuit 190 is arranged for determining the inductance of the coil 160. Here, the coil 170 is a cylindrical coil comprising windings 171 of electrically conductive wire, which wire is here wound around a bobbin 172. The coil 170 surrounds a hollow 173 (generally, the hollow 173 may be in the form of a through-hole or blind-hole and may have a regular, e.g. cylindrical shape, or may have an irregular shape). In some embodiments, the coil may be self-supporting (e.g. the coil may have been immersed in a resin so that the coil is stable without a bobbin). In the shown embodiment, the coil 170 is fixedly mounted with respect to the handle 140. The inductance of the coil 170 is changed when a coil core element 180 is moved in close proximity to the hollow 173 or even into or out of the hollow 173. In the shown embodiment, the coil core element 180 is fixedly mounted at the treatment head 120, more precisely at the arm element 122 extending from the pivot axis 150 towards the back end 149 of the personal hygiene device 100. The location of the coil core element 180 as shown shall not be construed as limiting and any other suitable location can also be chosen. The inductance of the coil 170 depends, inter alia, on the permeability of the material placed into or close to the hollow 173. As the coil core element 180 is fixedly mounted with respect to the treatment head 120 and the coil 170 is fixedly mounted with respect to the handle 140, the change of the coil inductance is indicative of the deflection angle of the treatment head 120 and thus of the applied treatment force F. Generally, the coil may also be fixedly mounted with respect to the treatment head and the coil core element may be fixedly mounted with respect to the handle, so that the same relative movement is induced.

In some embodiments, the coil core element is spring-mounted with respect to e.g. the handle and the treatment head, when being deflected, may act onto the coil core element to move it against the spring force and the spring force pushes back the coil core element when the treatment head (or a respective arm element) releases its impact on the coil core element.

Further, FIG. 2 indicates that in some embodiments, additional components may be present such as, e.g., an automatic adjustment circuit 191, a user-input unit 192, a transmitter unit 193 for establishing at least a one-directional wireless connection with an external device for transmitting data from the personal hygiene device to the external device, e.g. for displaying certain information, or an indication element 194, for e.g. visually, audibly, or in a tactile manner indicating information at the personal hygiene device 100. The indication element may be realized as a LED, loudspeaker, or a vibrator. These aspects will be further described in below paragraphs "Consumer adjustment of pre-determined treatment force threshold value" and "Automatic adjustment of the pre-determined threshold".

Figure 3A:
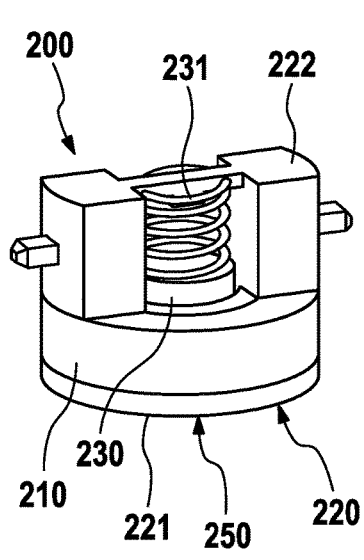
FIGS. 3A-B show schematic depictions of a compact assembly of a coil and a coil core element.
Figure 3B:
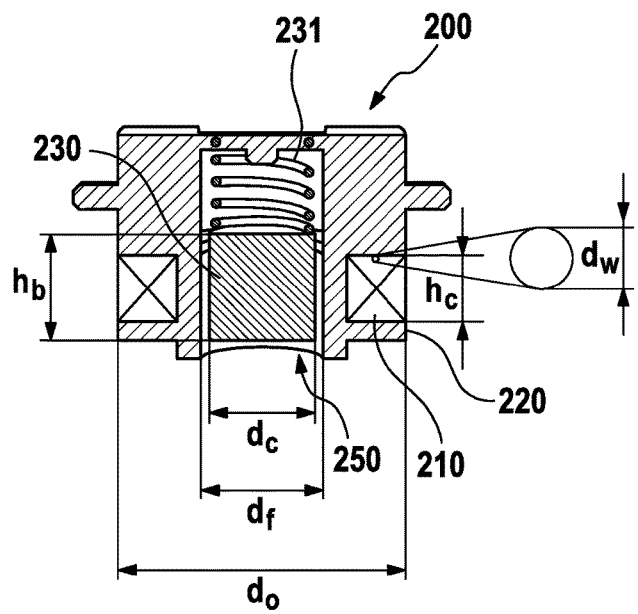

FIG. 3A shows an example embodiment that realizes a coil plus coil core element unit 200 in a compact assembly and FIG. 3B shows a cross-sectional cut through the assembly of FIG. 3A. The shown coil plus coil core element unit 200 comprises a coil 210, a bobbin 220, and a coil core element 230 that is mounted by a resilient element 231 (here realized as a mechanical coil spring) at an upper portion 222 of the bobbin 220, so that the coil core element 230 can be moved into and out of the hollow 250 against and via the spring force provided by the resilient element 231. E.g. a projection provided at the treatment head may act onto the coil core element 230 when the treatment head is deflected and thus moves the coil core element 230 out of the hollow 250. When the treatment force applied at the treatment head decreases and the deflection of the treatment head is reduced, the resilient element 231 moves the coil core element 230 back into the hollow 250. Obviously, the neutral position of the coil core element may also be at another location the shown centric placement with respect to the coil, e.g. in the neutral position, the core coil element may be off-centric or even completely placed outside of the hollow.

Realization of the Coil

The following aspects of the coil are discussed with reference to FIG. 3B, but it is noted that the following essential geometric considerations are independent from the particular example shown in FIG. 3B. While a coil 210 as such seems to be a well-known component, the precise specification of a coil 210 for the present purpose requires some detailed understanding. First of all, adding a macroscopic electronic component such as a coil 210 to a personal hygiene device of a preferred size generates a need for finding an optimum geometry that serves the needs of the application and the needs of the available construction volume. E.g. the coil 210 may be required to not extend beyond usual components on a PCB, so that a height $h_b$ or $h_c$ (depending on whether the coil is mounted on a bobbin or is self-supporting) in the range of between 1 mm to 4 mm may be a sensible first geometry parameter (in particular, this height value $h_b$ or $h_c$ may be set to be in the range of about 2.6 mm±1.0 mm) The (outer) diameter $d_o$ of the in particular cylindrical coil 210 may as well be set to a value in the range of between 6 mm and 9 mm as a second geometry value (in particular, this value may be set to be 7 mm±0.5 mm) A free inner coil diameter $d_f$ may be chosen to lie in the range of between about 3 mm to about 5 mm (in particular, this value may be set to be 4 mm±0.5 mm) As the coil wire may be wound around a bobbin 221, a free inner diameter $d_f$ of the coil 200 may be the free inner diameter of the bobbin 221. As the current application requires that a voltage change at the coil 210 can be reliably measured when a coil core element 230 is moved in and out of the hollow 250 of the in particular cylindrical coil 210, an inductance value of at least about 1000 micro-Henry (μH) may be a sensible electrical parameter of the coil 210. In this context, a resistance of below about 100 Ohm (Ω) may as well be considered a sensible electrical parameter. In order to achieve a high inductance, a high number of coil windings should be achieved. With a given volume, the number of windings can only be varied by changing the coil wire diameter $d_w$. It has been found that the coil wire diameter $d_w$ may be chosen to lie in the range of between about 0.03 mm and about 0.1 mm (in particular, this value may lie in the range of between 0.03 mm and 0.08 mm, further in particular this value may be set to 0.06 mm±0.02 mm) Wires below a diameter of 0.03 mm are prone to breakage in an automated handling process. Wire diameters above 0.1 mm lead to a too low number of wire windings in the given volume of a coil as discussed in this paragraph. Copper may be chosen as coil wire material.

Table 1 summarizes minimum and maximum values that had been considered for the geometry of a cylindrical coil suitable in particular for use in a hand-held personal hygiene device such as an electric toothbrush and for the respective electrical parameters of the coil, where it is to be understood that the minimum geometry values do not necessary lead to the minimum electrical parameters. As is known, the inductance of the cylindrical coil is proportional to the square of the number of windings and to the cross sectional area of the coil. The last line shows an example where more medium values have been chosen and the resulting inductance is above 1000 μH and the resistance is below 100Ω. As mentioned, an even higher inductance can be achieved by decreasing the wire diameter from 0.05 mm chosen in the example to e.g. 0.03 mm, but this increase is to be balanced against trouble-free automated handling of the wire.

TABLE 1

| Example | Wire diameter [mm] | No. of windings | Inner coil diameter [mm] | Outer coil diameter [mm] | Height [mm] | Inductance [μH] | Resistance [Ω] |
|---|---|---|---|---|---|---|---|
| Min | 0.03 | 400 | 3.0 | 6.0 | 1.5 | 500 | 50 |
| Max | 0.07 | 600 | 6.0 | 10.0 | 4.0 | 1500 | 200 |
| Example | 0.05 | 500 | 3.7[1] | 6.0 | 1.6[2] | 1162 | 70 |

[1] in the example, the coil was wound onto a bobbin and the free inner coil diameter of the bobbin was 2.6 mm.
[2] the height $h_b$ of the coil assembly including the coil bobbin was 2.6 mm.

Realization of the Coil Core Element

Similarly as the coil, the coil core element is to be realized in a manner that supports the geometry requirements and the needs of the application. Thus, besides low manufacturing costs, the coil core element should provide for voltage changes (i.e. inductances changes resulting in such voltage changes) that enable reliably measuring the treatment force that is applied at the treatment head of the personal hygiene device. It is desirable to not only allow determining whether the treatment force is above or below a certain threshold value but also to allow determining whether the treatment force is between at least two such threshold values. The threshold values may in particular be pre-determined. Further below it is described that the pre-determined threshold value(s) may become automatically adjusted or may be adjustable by a user.

The diameter $d_c$ of the coil core element (measured in the same plane as or in a plane parallel to the free inner coil diameter $d_f$) obviously depends on the available free inner coil diameter so that the coil core element can reliably be moved in and out of the hollow surrounded by the coil and so that an (in particular automated) mounting of the coil core element with respect to the coil is enabled. Generally, a distance in the range of between 0.3 mm to 1.0 mm between the coil core element and the inner edge of the coil (or bobbin) has been found to be a sensible value for reliable assembly. The material from which the coil core element is at least partly made is chosen from the group of materials providing a sensibly high relative permeability µ/µ0, where the material shall have a relative permeability of at least 10, in particular of at least 100 and further in particular of at least 1000. Suitable materials may be chosen from the group of nickel, carbon-steel, ferrite (e.g. nickel-zinc ferrite: $Ni_aZn_{(1-a)}Fe_2O_4$ or manganese-zinc ferrite: $Mn_aZn_{(1-a)}Fe_2O_4$), annealed ferritic or martensitic stainless steel, iron, permalloy, mu-metal. Combinations of these materials are as well possible. The list is not complete and other materials may be chosen as well, e.g. cobalt-iron, 99.95% pure Fe annealed in H, Nanoperm®, Metglas®, etc. Iron and iron-based ferrites are relatively cheap, can be manufactured in arbitrary shapes (e.g. at least one undercut can be provided in the coil core element for connection with a holding structure, e.g. provided at an arm element of the treatment head), and provide a good relative permeability µ/µ0 of up to 10.000. In some embodiments, the coil core element is made from a sintered material.

In some embodiments the coil core element comprises at least one undercut or projection, e.g. for connecting the coil core element with a resilient element or a holder structure.

Realization of the Control Circuit

Figure 4:
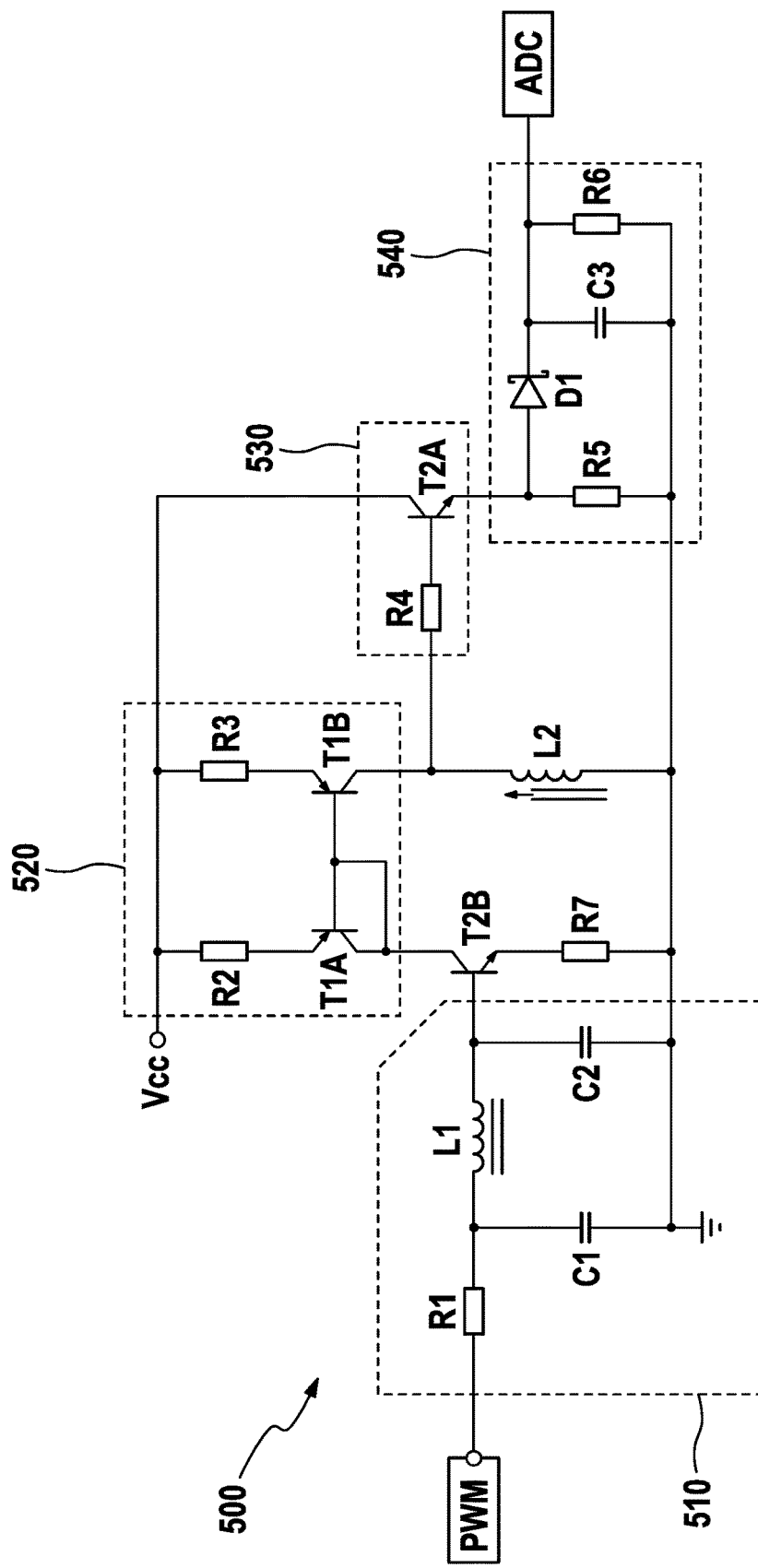
FIG. 4 is a depiction of an example embodiment of an electronic sub-circuit for measuring the inductance change of a coil when a coil core element is moved in and out of the coil hollow by determining a peak voltage change.

The treatment-force-measurement unit comprises a (electronic) control circuit for (directly or in particular indirectly) determining a parameter indicative of the inductance (or change of the inductance) of the coil (e.g. by determining as parameter a voltage or voltage change over the coil). The control circuit thus may comprise an electronic sub-circuit for applying an alternating voltage at the coil and for determining the average voltage developing over the coil. FIG. 4 shows an example embodiment of such an electronic sub-circuit 500. The control circuit may further comprise a microcontroller and/or an analog to digital converter (ADC). A microcontroller may be used to generate a pulse width modulated signal. An ADC may be used to digitize a voltage signal. In some embodiments, an ADC is comprised by a microcontroller. One example of a chip suitable for providing a PWM output and an ADC input is the system-on-chip CC2541 from Texas Instruments, Texas, USA.

The electronic sub-circuit 500 receives a square wave signal PWM at a given frequency and with a given duty cycle (the PWM signal may be provided by a microcontroller or a dedicated electronic circuit). In some embodiments, the duty cycle may be set to 50% and the frequency may be set to 30 kHz. But other suitable values may be chosen as well. In order to avoid audible resonance, the frequency may be chosen to be above 20 kHz. The frequency also may be set in dependence on the material of the coil core element. E.g. for a coil core element made from iron, a range of between 25 kHz and 35 kHz may be chosen, but for ferrites and other materials allowing a relatively fast reversion of the magnetization direction, frequencies of up to 100 kHz or even more may be feasible. The electronic sub-circuit 500 comprises a filter circuit 510, here a low pass filter of third order that comprises a resistor R1, two capacitors C1 and C2 and an inductance L1, which filter circuit 510 transforms the square wave signal PWM into an alternating voltage signal approximating a sine wave. A current mirror circuit 520 here comprising two resistors R2 and R3 and two transistor elements T1A and T1B amplifies the respective sine wave current and thus drives a defined sine wave current through the coil L2, which represents the coil discussed before whose inductance is varied by moving a coil core element into and out of the coil hollow (the inductance change leads to a change of the impedance of the coil, which impedance influences the voltage at the coil in accordance with the complex Ohmic law $U=I \cdot Z$, where U is the voltage, I is the current, and Z is the complex impedance, which depends on the inductance of the coil L2). As the current mirror circuit 520 drives the current (which is thus not influenced by the characteristics of the coil L2), the variable impedance of coil L2 results in an accordingly varying voltage over the coil L2, which voltage is fed into an amplification circuit 530 that comprises a resistor R4 and a transistor T2A. A rectification and peak voltage detection circuit 540 that comprises a diode D1, two resistors R5 and R6 and a capacitor C3, receives the voltage that develops over the coil L2. The alternating coil voltage is rectified and the peak voltage value is finally provided as output of the whole electronic sub-circuit 500. The peak voltage value is representative of the impedance of the coil L2 and thus representative of the treatment force applied at the treatment head, as the treatment force is translated into a movement of the coil core element relative to the coil hollow as has been described before. This peak voltage value can e.g. be input into an ADC of the control circuit for generating a digital signal, but it is also contemplated that the analogue peak voltage signal is used and e.g. fed into one or several comparators.

The control circuit may be arranged to provide a signal when the applied treatment force reaches a pre-determined first threshold force value or to provide particular signals when the applied treatment force reaches (i.e. crosses) one of several pre-determined treatment force threshold values. The pre-determined treatment force threshold value(s) may be adjustable as will be discussed in the following. Based on the signals from the control circuit, it can be indicated to the user, e.g., via an indication element whether a treatment force in a certain range is applied, e.g. by use of differently colored light emitting elements or via an audible or tactile signal. In addition, a time series of applied treatment force values may be recorded by the control circuit and the control circuit may be arranged to perform an analysis of the time series of treatment force values, e.g. in order to indicate to the user how long a correct treatment force was applied during a treatment session, optionally for how long a too high treatment force was applied, and further optionally how long a too low treatment force was applied. The personal hygiene device may comprise as indication element a display for providing this kind of information or the personal hygiene device may comprise a transmitter unit for wireless communication with an external device (e.g. a computer, tablet, or smartphone), which external device may then display the information and/or store the time series of treatment force values and perform said analysis.

Examples of Measurement Results

In the following, some example measurement results are discussed with reference to FIGS. 5A and 5B. In these figures, peak voltage curves are plotted vs. the immersion depth of a coil core element into a hollow surrounded by a coil, where the coil used for the measurement had a free inner diameter of 3.7 mm (free inner diameter of bobbin: 2.7 mm), a height of 1.6 mm (the height together with bobbin was 2.6 mm), and 500 windings made from copper wire of 0.05 mm diameter (same values as given in above Table 1). An electronic sub-circuit as shown in FIG. 4 had been used and an alternating current signal was applied at the coil with a frequency of 29.4 kHz and a duty cycle of 50%. In the graphs, the immersion depth $d_i$ in millimeter is given on the x-axis and the peak voltage $V_p$ in Volts is given on the y-axis. The immersion depth $d_i$ starts at 0 mm when the coil core element starts to immerse into the coil hollow defined by the top bobbin wall (see FIG. 3B), so that the first 0.5 mm immersion depth are just an immersion into the bobbin, not into the coil itself—see curve C10 in FIG. 5B, where the maximum of the peak voltage is correspondingly at $d_i$=2.3 mm (i e the 2 mm coil core element had to be immersed into the hollow by 2.3 mm to be placed symmetrically with respect to the coil). A negative immersion depth means that the coil core element had a distance to the coil hollow.

The movement length of the coil core element relative to the coil hollow obviously depends on the chosen geometry and the occurring force (and on the stoppers, if such are used, and on the biasing spring force against which the treatment head is moved), but for personal hygiene devices, the available space in the housing of such a device is limited and a typical movement length in the range of between 0.25 mm to 5 mm may be chosen, in particular a range of between 0.5 mm and 2 mm. In some embodiments, the movement length is 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm etc. It was found that a peak voltage difference of at least about 50 mV over the movement length of the coil core element would be desirable in order to enable a decent analysis of the treatment force. The peak voltage difference may in particular be chosen to be at least 75 mV, 100 mV, 125 mV, 150 mV, 175 mV, 200 mV, 225 mV, 250 mV or even higher.

Figure 5A:
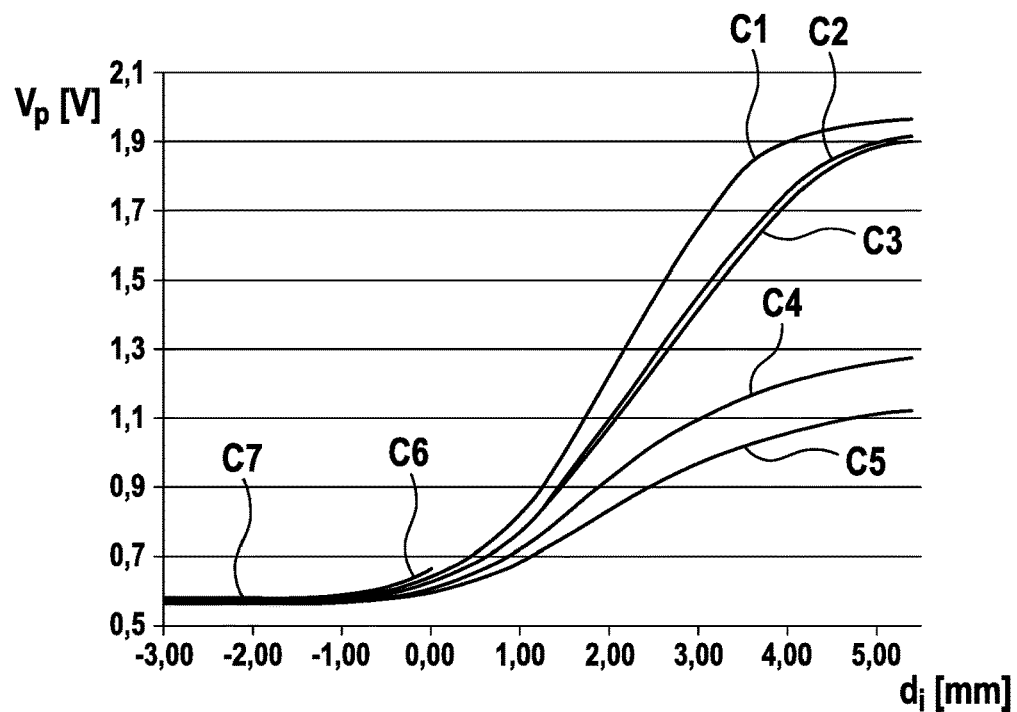
FIGS. 5A-B are depictions of peak voltage curves measured by an electronic sub-circuit as shown in FIG. 4, where the peak voltage is plotted against the penetration depth of the coil core element under various conditions such as coil core element material, diameter, and length.

In FIG. 5A the influence of the material (i.e. the relative permeability) and the diameter of the coil core element was investigated (curves C1, C3, C4, and C5) and also the influence of a non-concentric immersion of a coil core element into the coil hollow (curve C2). Here, curve C1 relates to a ferrite rod having a 2.0 mm diameter, curve C3 relates to a ferrite rod of 1.5 mm diameter, curve C4 relates to an iron rod of 2 mm diameter, and curve C5 relates to an iron rod of 1.5 mm diameter. Curve C2 relates to the rod of curve C3, but the rod was immersed in an off-centric manner (a 0.4 mm offset was applied). In addition, iron discs larger in diameter than the inner coil diameter were used (curves C6 and C7, which curves end at immersion depth of $d_i$=0.0 mm as these large discs could not be immersed into the coil hollow). Curve C6 relates to a disc of 8 mm diameter and a thickness of 0.7 mm Curve C7 relates to a disc with 9 mm diameter and a thickness of 0.3 mm. The length of the coil core element used in these tests (curves C1 to C5) was much longer than the coil height so that the voltage does not drop even for the highest immersion depth. It can generally be seen in FIG. 5A that the voltage change is relatively low before the coil core element start immersion into the coil hollow at immersion depth of 0.0 mm. The voltage curves start to become almost linear at an immersion depth of 1.0 mm for the discussed coil geometry. It can be seen that for the coil core element curves C1 to C5, a peak voltage difference of around 70 mV can already be achieved with a 1.5 mm diameter iron rod when a start immersion depth in the almost linear part of the curves is chosen and the rod is then further moved into the coil hollow with a movement length of 1 mm With a 2 mm ferrite rod, a much higher peak voltage difference of up to about 210 mV can be achieved. It was also concluded that coil core elements that do not immerse into the coil hollow only generate a peak voltage difference of below 50 mV for a movement length of 1 mm (e.g. from −1 mm to 0 mm) But it is expected that with a ferrite disc or another high relative permeability material and some adaptations to the electronic sub-circuit, also embodiments with non-immersing coil core elements can reach a 50 mV peak voltage difference. In embodiments with a self-supporting coil (i.e. without bobbin), also higher peak voltage differences are possible without an immersion into the coil hollow. Embodiments with a partly-immersed coil core element at a start immersion depth lying in the almost linear part of a peak voltage curves also tolerates manufacturing variations, i.e. differences in the starting immersion depth, as the approximately linear behavior leads to almost the same peak voltage difference while being in the almost linear part independent from the precise starting immersion depth. Thus, in some embodiments, the immersion depth of the coil core element in the rest position is chosen to lie in an almost linear portion of the peak voltage curve and it may be arranged that the deflection of the treatment head moves the coil core element in such a manner that the resulting peak voltage remains in the almost linear portion of the peak voltage curve.

Figure 5B:
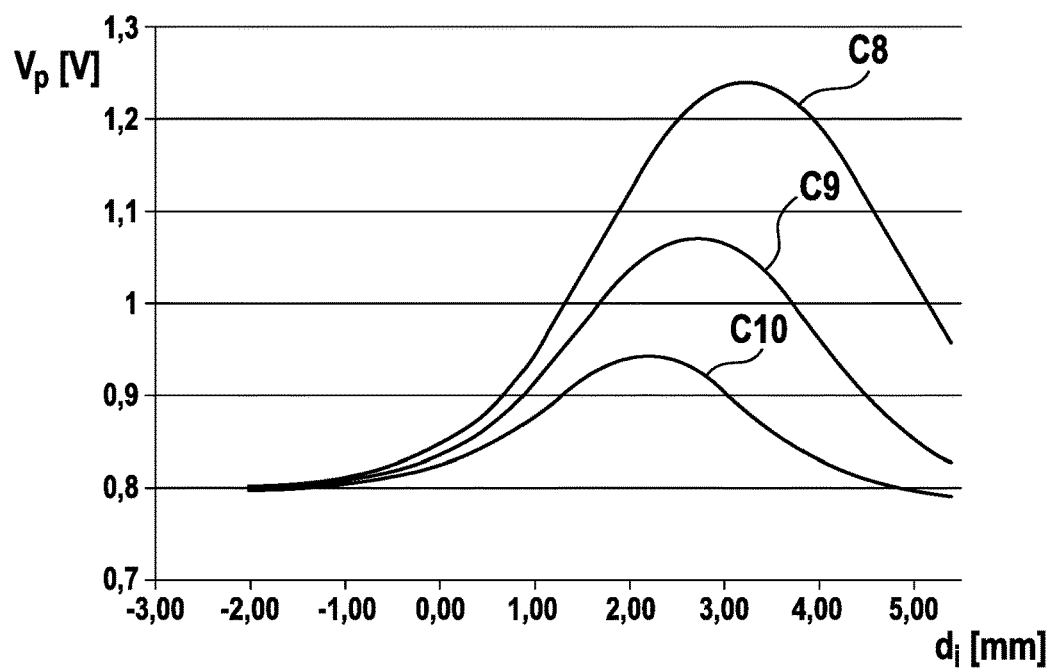

In FIG. 5B the influence of the length of the coil core element at constant diameter and constant material was investigated. The curves relate to a ferrite rod with 1.5 mm diameter and a length of 4 mm (curve C8), 3 mm (curve C9), and 2 mm (curve C10), respectively. As expected, Gaussian-type of curves result, which curves have their peak-voltage maximum when the coil core element is symmetrically immersed into the coil hollow (at $d_i$=3.3 mm for curve C8, at $d_i$=2.8 mm for curve C9, and at $d_i$=2.3 mm for curve C10). It can be seen that the length of the coil core element has a strong influence on the resulting peak-voltage curves. But already with a 2 mm long ferrite rod, a peak voltage difference between immersion depths of 1 mm and 2 mm of about 90 mV can be achieved in the chosen setup. The longer ferrite rods provide for a higher peak voltage difference and also for a wider range of approximately linear behavior tolerable to manufacturing tolerances.

Calibration

It is contemplated that the personal hygiene device as disclosed herein may be calibrated, e.g. at the plant of the manufacturer. A series of at least two or more precisely controlled load values may be applied at the treatment head so that the treatment-force-measurement unit can calibrate the values of the parameter indicative of the inductance of the coil (e.g. peak voltage values over the coil) measured by the control circuit versus the applied force values. The personal hygiene device may be provided with a particular calibration mode in which the respective force values to be applied during calibration are pre-programmed and the parameter values which are measured during the calibration procedure are then used for a respective calibration. In an alternative or additional embodiment, the personal hygiene device can communicate with an external device (a wired or wireless connection may be used) via which the applied load values are communicated from the external device to the personal hygiene device for using these values in the calibration. Alternatively or additionally, the measured peak voltage values may be communicated from the toothbrush to the external device, which then performs the calibration and communicates back calibration parameters to be applied. In the latter embodiment, a complex calibration circuit is not necessary in the personal hygiene device.

Consumer Adjustment of Pre-Determined Treatment Force Threshold Value

The personal hygiene device may be equipped with a user-input unit for adjusting at least one of the pre-determined treatment force threshold values (or for adjusting the pre-determined treatment force threshold value if only one such value is set). Such a user-input unit may be realized as a simple switch or as a touch-sensitive pad. In some embodiments, the user-input unit is realized as a wireless connectable receiver or transceiver for receiving (and optionally transmitting) data between an external device (e.g. a smartphone onto which a suitable application was loaded) and the personal hygiene device. In the latter embodiment, comfortable and manifold setting possibilities can be realized without the need to realize the respective complex user-input unit in the personal hygiene device.

Automatic Adjustment of the Pre-determined Threshold

Two different possible examples of an automatic adjustment of at least one pre-determined treatment force threshold value are discussed. In the first example, the personal hygiene device is arranged for an automatic adjustment when a treatment mode of the personal hygiene device is changed. E.g. in case of toothbrushes, it is known to provide different brushing modes such as "Standard Cleaning Mode", "Soft Cleaning Mode", or "Gum Care Mode". While the pre-determined treatment force threshold value for the applied treatment force may be set to 3 N for the "Standard Cleaning Mode", the pre-determined treatment force threshold value may be changed to 2.5 N in case the "Soft Cleaning Mode" is chosen or e.g. to 2.0 N if the "Gum Care Mode" is chosen. Depending on the chosen treatment mode, the device can then indicate a dedicated too high treatment force. In the second example, the personal hygiene device (in particular the treatment-force-measurement unit) is arranged to measure a time series of applied treatment force values and to automatically adjust the pre-determined treatment force threshold value(s) based on the habits of the user. An automatic adjustment unit may be provided for performing the mentioned automatic adjustments.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal hygiene device comprising:
    a handle;
    a treatment head mounted for relative movement with respect to the handle against a spring force when a treatment force is applied in at least one direction onto the treatment head;
    a treatment-force-measurement unit for determining the applied treatment force comprising an electrically powered coil, a coil core element, and a control circuit for determining a parameter indicative of the inductance of the coil;
    wherein the coil core element is arranged to be moved with respect to a hollow of the coil when the treatment head is moved, and
    wherein the coil core element has a diameter measured in the same direction as a diameter of the hollow is measured, wherein the diameter of the coil core is from about 0.3 mm to about 1.0 mm smaller than the diameter of the hollow.

2. The personal hygiene device in accordance with claim 1, wherein
    the treatment-force-measurement unit comprises an arm element fixedly secured with respect to or integral with the treatment head;
    the coil is fixedly secured with respect to either the arm element or the handle;
    the coil core element is positioned at least partly in or close to the hollow surrounded by the coil; and
    the arm element is arranged to move one of the coil and the coil core element so that the coil core element is moved into or out of the hollow when the treatment force is applied.

3. The personal hygiene device in accordance with claim 1, wherein the coil core element is spring-mounted with respect to the handle.

4. The personal hygiene device in accordance with claim 1, wherein the coil has a height between about 1 mm and about 3 mm.

5. The personal hygiene device in accordance with claim 4, wherein the outer diameter of the coil is not larger than about 10 mm.

6. The personal hygiene device in accordance with claim 4, wherein an inner free diameter of the coil is in between about 3.0 mm and about 5.0 mm.

7. The personal hygiene device in accordance with claim 1, wherein the coil has between about 400 and about 600 windings.

8. The personal hygiene device in accordance with claim 1, wherein a first stopper is fixedly provided with respect to the handle against which the treatment head abuts when no treatment force is applied at the treatment head.

9. The personal hygiene device in accordance with claim 8, wherein the treatment head is spring-biased and is arranged to move away from the first stopper when a treatment force above a first treatment force threshold value is applied at the treatment head.

10. The personal hygiene device in accordance with claim 8, wherein a second stopper is fixedly provided with respect to the handle against which the treatment head abuts when a treatment force having a second treatment force threshold value is applied at the treatment head.

11. The personal hygiene device in accordance with claim 1, wherein the control circuit is arranged to provide at least one signal when the coil inductance indicates that at least one of pre-determined treatment force threshold values is reached.

12. The personal hygiene device in accordance with claim 11, comprising a user-input unit for adjusting the at least one of the pre-determined treatment force threshold values.

13. The personal hygiene device in accordance with claim 11, wherein the control circuit is arranged to record values of the applied treatment force.

14. The personal hygiene device in accordance with claim 13, wherein the control circuit is arranged to adjust at least one of the pre-determined values based on a history of the recorded applied treatment force values.

15. The personal hygiene device in accordance with claim 11, wherein the control circuit is arranged to provide information selected from the group consisting of brush time relating to an applied treatment force below the pre-determined treatment force threshold value, brush time relating to an applied treatment force above the respective pre-determined value, brush time between at least one of the pre-determined treatment force threshold values and a further one of the pre-determined treatment force values, and any combination thereof.

16. The personal hygiene device in accordance with claim 11, comprising an automatic adjustment unit for automatically adjusting the at least one of the pre-determined treatment force threshold values.

17. The personal hygiene device in accordance with claim 1, wherein the coil core element is at least partly made from a coil core material that has a relative permeability $\mu/\mu_o$ of at least 10 and wherein the coil core material is selected from the group consisting of nickel, carbon-steel, ferrite, annealed ferritic or martensitic stainless steel, iron, permalloy, mu-metal, and any combination thereof.

18. The personal hygiene device in accordance with claims 1, further comprising a transmitter unit for establishing a wireless connection.

19. The personal hygiene device in accordance with claim 1, wherein a wire diameter of the coil is between about 0.03 mm and about 0.1 mm.

* * * * *